United States Patent [19]

Alston et al.

[11] Patent Number: 5,861,540

[45] Date of Patent: *Jan. 19, 1999

[54] SUBSTITUTED 1,1,1-TRIARYL-2,2,2-TRIFUOROETHANES AND PROCESSES FOR THEIR SYNTHESIS

[75] Inventors: William B. Alston, Medina, Ohio; Roy F. Gratz, Fredericksburg, Va.

[73] Assignee: The United States of America as represented by the Administrator of the National Aeronautics and Space Administration, Washington, D.C.

[ * ] Notice: The terminal 32 months of this patent has been disclaimed.

[21] Appl. No.: 228,541

[22] Filed: Apr. 15, 1994

Related U.S. Application Data

[62] Division of Ser. No. 982,350, Nov. 27, 1992, abandoned, which is a division of Ser. No. 822,240, Jun. 17, 1992, Pat. No. 5,334,733, which is a division of Ser. No. 545,088, Jun. 28, 1990, abandoned, which is a division of Ser. No. 419,554, Apr. 30, 1991, Pat. No. 5,011,955, which is a division of Ser. No. 292,049, Dec. 30, 1988, Pat. No. 4,912,238, which is a division of Ser. No. 159,071, Feb. 23, 1988, Pat. No. 4,885,116, which is a division of Ser. No. 924,474, Oct. 19, 1986, Pat. No. 4,758,380.

[51] Int. Cl.[6] .................................................. C07C 19/08

[52] U.S. Cl. ............................. 570/129; 568/16; 568/34; 568/56; 568/332; 568/639; 564/322

[58] Field of Search .............................. 570/129; 568/639, 568/56, 34, 16, 332; 564/322

[56] References Cited

U.S. PATENT DOCUMENTS 4,742,152  5/1988  Scola ........................................ 528/353

*Primary Examiner*—Jose G. Dees
*Assistant Examiner*—Samuel Barts
*Attorney, Agent, or Firm*—Kent N. Stone; Guy M. Miler

[57] ABSTRACT

Synthetic procedures to tetraalkyls, tetraacids and dianhydrides substituted 1,1,1-triaryl-2,2,2-trifuoroethanes which comprises: (1) 1,1-bis(dialkylaryl)-1-aryl-2,2,2-trifluoroethane, (2) 1,1-bis(dicarboxyaryl)-1-aryl-2,2,2-trifluoroethane or (3) cyclic dianhydride or diamine of 1,1-bis(dialkylaryl)-1-aryl-2,2,2-trifluoroethanes. The synthesis of (1) is accomplished by the condensation reaction of an aryltrifluoromethyl ketone with a dialkylaryl compound. The synthesis of (2) is accomplished by oxidation of (1). The synthesis dianhydride of (3) is accomplished by the conversion of (2) to its corresponding cyclic dianhydride. The synthesis of the diamine is accomplished by the similar reaction of an aryltrifluoromethyl ketone with aniline or alkyl substituted or disubstituted anilines. Also, other derivatives of the above are formed by nucleophilic displacement reactions.

3 Claims, 3 Drawing Sheets

```
┌─────────────────────────────────────┐
│      TETRAALKYL – SUBSTITUTED       │
│ 1,1,1, – TRIARYL – 2,2,2, – TRIFLUOROETHANE │
│             COMPOUND                │
└─────────────────────────────────────┘
           │ HNO$_3$
           │ [O]
           │
┌─────────────────────────────────────┐
│ 1,1 – BIS (DICARBOXYARL) – 1 – (3 – NITROARYL) – 2,2,2 │
│           – TRIFLUOROETHANE         │
└─────────────────────────────────────┘
           │ NUCLEOPHILIC
           │ DISPLACEMENT REACTION
           │
           │ (Y RADICAL CONTAINING
           │ NUCLEOPHILIC REAGENT)
           │
┌─────────────────────────────────────┐
│ 1,1 – BIS (DICARBOXYL – 1 – (3 – Y ARYL) – 2,2,2 │
│           – TRIFLUOROETHANE         │
└─────────────────────────────────────┘
```

FIG. 3

SUBSTITUTED 1,1,1-TRIARYL-2,2,2-TRIFUOROETHANES AND PROCESSES FOR THEIR SYNTHESIS

This application is a division of application Ser. No. 07/982,350, filed Nov. 27, 1992, and now abandoned, which is a division of application Ser. No. 07/822,240, filed Jun. 17, 1992, and issued as U.S. Pat. No. 5,334,733, which is a division of application Ser. No. 07/545,088, filed Jun. 28, 1990, and now abandoned, which is a division of application Ser. No. 07/419,554, filed Apr. 30, 1991, and issued as U.S. Pat. No. 5,011,955, which is a division of application Ser. No. 07/292,049, filed Dec. 30, 1988, and issued as U.S. Pat. No. 4,912,238, which is a division of application Ser. No. 07/159,071, filed Feb. 23, 1988, and issued as U.S. Pat. No. 4,885,116, which is a division of application Ser. No. 06/924,474, filed Oct. 19, 1986, and issued as U.S. Pat. No. 4,758,380.

ORIGIN OF THE INVENTION

The invention was made by Government employees and may be manufactured or used by or for the Government without the payment of any royalties thereon or therefor.

BACKGROUND OF THE INVENTION

1. Field of the Invention

The present invention relates to methods for the synthesis of substituted 1,1,1-triaryl-2,2,2-trifluoroethanes and to products resulting therefrom, as well as to derivatives derived from said products. The polymeric derivatives of said products meet or exceed the performance characteristics required for high temperature resins and composites in present or future aeronautic requirements.

The utility of polyimides as a class of polymers is well-known. Polyimides, because of their low cost, excellent thermo-oxidative stability, chemical stability, and commercial availability, are in a class by themselves. They exhibit widespread applications, such as for films, coatings, moldings, adhesives, binder solutions and matrix resins. Extensive review articles and books, such as in Heat-Resistant Polymers, J. P. Critchley, et al, chapter 5, on Polyimides, (Plenum Press, 1983) describe the many polyimides that have been prepared and indicate which compositions are successful commercial variants. In a class by themselves are the fluorinated containing 1,1,1,3,3,3-hexafluoroisopropylidene (6F) polyimides because of their superior thermal stability compared to non-fluorinated polyimides. The 6F containing polyimides have become the state-of-the-art in melt processable polyimides for moldings and matrix resin applications. This patent application is designed to show new synthetic routes for the new 1,1,1-triaryl-2,2,2-trifluoroethane (3F) containing monomers which will exhibit all the desirable melt fusible-melt processable characteristics of 6F containing monomers but in addition are more versatile than 6F containing monomers because of the potentials described to introduce a variety of functional groups for the modification of polymer properties. In addition, this disclosure claims a variety of methods to effect the functional group introduction, such as from during the initial monomer synthesis, to during a later step in the monomer synthesis, to performing functional group changes on the final polymer structure. The copending Lew 14,346-1 disclosure generally claims the polymerization to new 3F polyimides after the functional groups for modifying polymer properties are already within the monomer structure but is not limited to introduction of functional groups prior to polymerization changes in functional groups may be effected once a functional group already exists within a 3F containing polymer.

2. Description of the Prior Art

Presently, one method of meeting high temperature performance requirements has been through the use of commercially available thermo-oxidatively stable monomers/polymers based on a 2,2-diaryl-1,1,1,3,3,3-hexafluoroisopropylidene structure (6F). A 1,1,1-tri-aryl-2,2,2-trifluoroethane structure (3F) is also known.

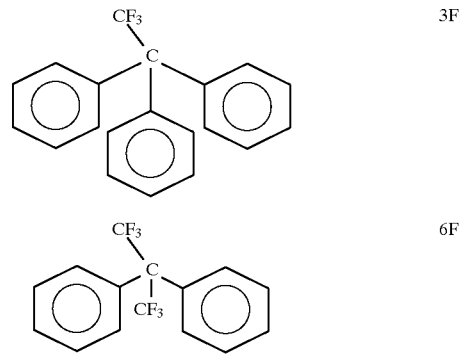

The synthesis of dianhydrides and diamines based on similar 6F structures has been previously reported as follows and is described within examples in U.S. Pat. No. 3,310,573, which issued on Mar. 21, 1967.

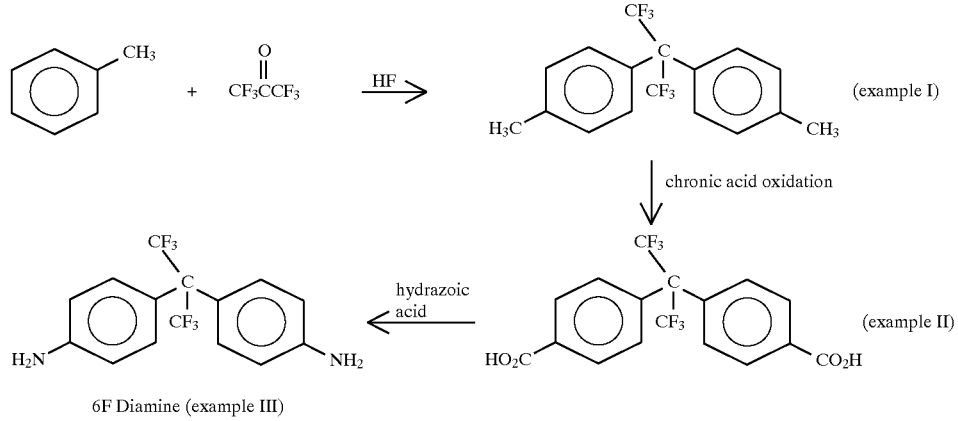

6F Diamine (example III)

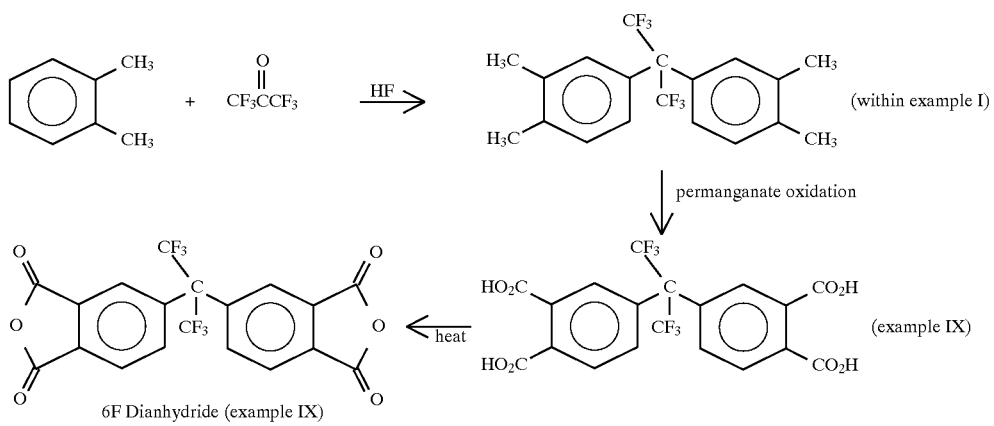
(within example I)

(example IX)

6F Dianhydride (example IX)

The dianhydride of example IX of U.S. Pat. No. 3,310, 573 is presently used in commercially available resin products (called NR 150 resins) available from E. I. dupont. The 6F dianhydride and 6F diamine monomers are also presently available in developmental quantities from American Hoechst. A similar 6F diamine with meta, rather than para, substitution has been recently synthesized, K. S. Y. Lau, et al., J. Polymer Science, 20, 2381–2393 (1982), and is also available from American Hoechst in developmental quantities. The synthesis of this diamine is summarized below.

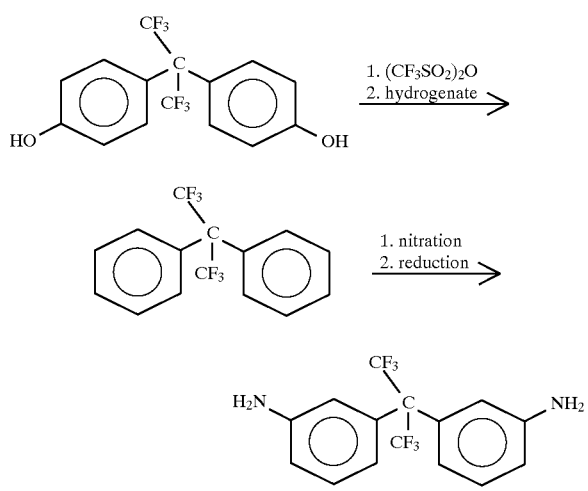

The synthesis of similar diamines but based on a 3F structure through a different synthetic route has been reported using aniline with an anilinium hydrochloride catalyst, by W. D. Kray and R. W. Rosser, J. Org. Chem., 42, 1186–1189 (1977).

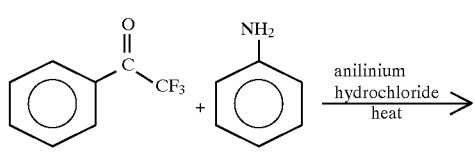

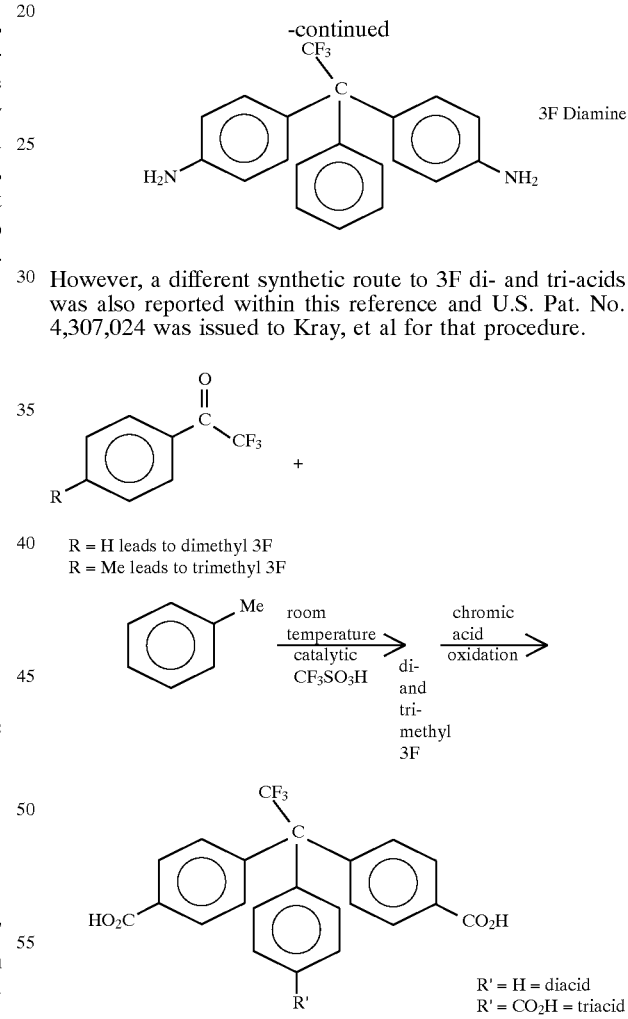

3F Diamine

However, a different synthetic route to 3F di- and tri-acids was also reported within this reference and U.S. Pat. No. 4,307,024 was issued to Kray, et al for that procedure.

R = H leads to dimethyl 3F
R = Me leads to trimethyl 3F

R' = H = diacid
R' = CO$_2$H = triacid

However, neither of the Kray, et al references describe the synthesis of a tetra substituted 3F structure required to prepare a new 3F dianhydride monomer. Nor do these references describe the requirement to use stoichiometric, rather than catalytic, amounts of CF$_3$SO$_3$H condensing agent based on equimolar or greater amounts of CF$_3$SO$_3$H with the aryl trifluoromethyl ketone.

The utility of the synthesis of 3F monomers over state-of-the-art 6F monomers is because the 3F phenyl ring is useful as a synthetic site. This utility creates 3F synthesis technology as the next generation of more synthetically versatile polymers compared to the state-of-the-art 6F polymers currently claimed for specialized applications such as solar cell coatings (U.S. Pat. No. 4,592,925) or radiation-resistant or radiation sensitive modified 6F monomers (U.S. Pat. No. 4,416,973). A further utility of 3F monomers over non-3F or 6F monomers/polymers is in the synthetic procedure to prepare 2,6-substituted and disubstituted 3F diamines for potential use as photoresists. This advances the technology of non-fluorinated photoresists described in J. Pfeifer and O. Rhode of Ciba-Geigy in "Direct Photoimaging of Fully Imidized Solvent Soluble Polyimides" in proceedings of 2nd International Conference on Polyimides, 10/30/85–11/1/85 at Ellenville, N.Y.

SUMMARY OF THE INVENTION

Therefore, it is an object of this invention to provide a process for preparing tetraalkyl-substituted 1,1,1-triaryl-2,2,2-trifluoroethanes, which comprises reacting an aryl trifluoromethyl ketone with a dialkylaryl compound.

A further object is to provide methods for preparing tetracarboxy-substituted 1,1,1-triaryl-2,2,2-trifluoroethanes, which comprises oxidation of a 1,1-bis(dialkylaryl)-1-aryl-2,2,2-trifluoroethane compound.

A further object is to provide methods for preparing cyclic dianhydrides of 1,1,1-triaryl-2,2,2-trifluoroethane, which comprises conversion of a 1,1-bis(dicarboxyaryl)-1-aryl-2,2,2-trifluoroethane compound to its corresponding cyclic dianhydride.

A further object is to provide a method for preparing diamines of 1,1,1-triaryl-2,2,2-trifluoroethane.

A further object is to provide a method for preparing tetracarboxy-substituted 1,1,1-triaryl-2,2,2-trifluoroethanes, which additionally contain pendant fragments substituted nucleophilicly thereon.

Yet further we have discovered that the products resulting from each of the above methods are new.

Further objects of the invention will be apparent from the detailed description of the invention which follows.

DETAILED DESCRIPTION OF THE INVENTION AND PREFERRED EMBODIMENTS

Tetraalkyl-Substituted 1,1,1-Triaryl-2,2,2-Trifluoroethanes

Applicants have discovered a novel process for reacting an aryl trifluoromethyl ketone with a dialkylaryl compound which will result in the formation of a new tetraalkyl-substituted 1,1,1-triaryl-2,2,2-trifluoroethane compound.

Suitable aryl trifluoromethyl ketones include those of the formula

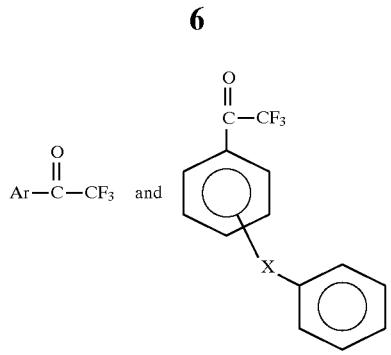

wherein Ar=cyclic and polycyclic aromatic hydrocarbons such as benzene, naphthene, phenanthrene, pyrene, anthracene, etc. and X is O (oxygen), S (sulfur), $SO_2$ (sulfone), NH (nitrogen-hydrogen), PH (phosphorous-hydrogen), NØ (nitrogen- phenyl), PØ (phosphorous-phenyl), C=O (carbonyl), $CH_2$ (methylene) or CHØ (carbon-hydrogen-phenyl) and the placement of X may be in either the meta or para positions.

Especially preferred is α,α,α-trifluoroacetophenone,

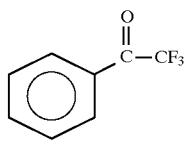

As to the dialkyl compound, the one preferred is O-xylene,

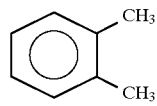

The process comprises a condensation type reaction. The preferred process additionally comprises utilization of a stoichiometric amount of a condensation catalyst, wherein the reaction is conducted at room or heated temperatures. The process especially preferred additionally comprises utilization of a stoichiometric amount of a condensation catalyst comprising trifluoromethyl sulfonic acid based on molar amount of aryltrifluoromethyl ketone, wherein the reaction is conducted at room temperature. The process is illustratively shown as follows and is described in example I.

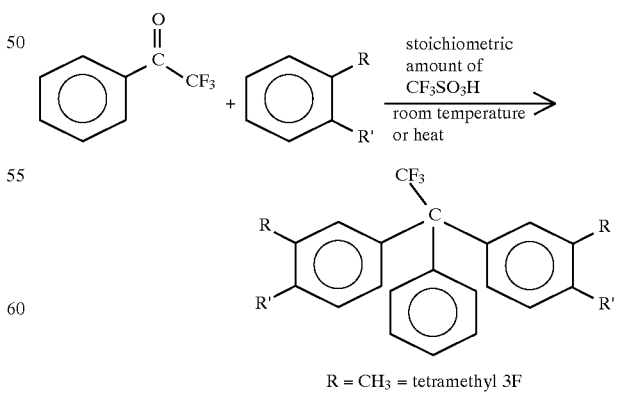

R = $CH_3$ = tetramethyl 3F

The alkyl groups R and R' are the same or different and may be but are not limited to methyl, ethyl, isopropyl, propyl, t-butyl, n-butyl, isobutyl, etc. The only limitation being that the R,R' containing compound be liquid at the reaction temperature to act as the reaction solvent. A general description of the typical aryltrifluoromethyl ketone condensation process is as follows:

An aryltrifluoromethyl ketone, where aryl is a phenyl, polycyclic aromatic hydrocarbon or phenyl with a pendant non-alkyl group attached, is reacted with an excess an ortho-substituted dialkyl aromatic using an equimolar or greater amount (based on moles of aryltrifluorometyl ketone) of organic superacids, such as trifluoromethyl-sulfonic acid. The solvent for the reaction is always the ortho-substituted dialkyl aromatic. The condensation reaction may be done between °C. and the reflux temperature of solvent for anywhere from 1 hour to 7 days, however the preferred choice is at least 2 days at room temperature (20°–25° C). The product invariably precipitates from the reaction mixture and is isolated by filtration. A second crop of product is often obtained by evaporation of the reaction filtrate. The yields may be from 0 to 100%, but generally range from 70 to 80% of tetraalkyl substituted 1,1,1-triaryl-2,2,2-trifluoroethanes.

Tetracarboxy-Substituted 1,1,1-Triaryl-2,2,2-Trifluoroethanes

Applicants have also discovered a novel process which comprises oxidation of a tetraalkyl-substituted 1,1,1-triaryl-2,2,2-trifluoroethane compound to produce a new tetracarboxy-substituted 1,1,1-triaryl-2,2,2-trifluoroethane compound.

Suitable tetraalkyl-substituted 1,1,1-triaryl-2,2,2-trifluoroethane compounds include those of the formula:

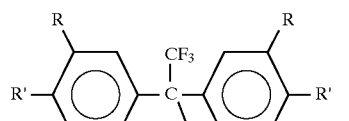

and

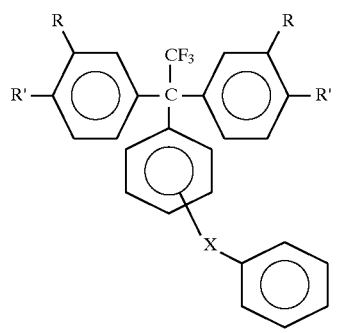

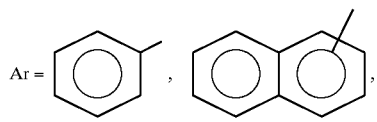

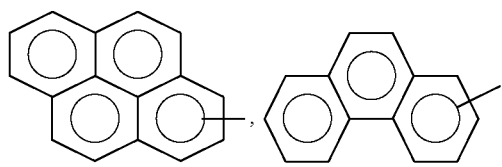

and larger polycyclic aromatics wherein X is O, S, $SO_2$, NH, PH, N∅, P∅, C═O, $CH_2$ or CH∅ and R,R'=an alkyl chain as described above. Especially preferred is

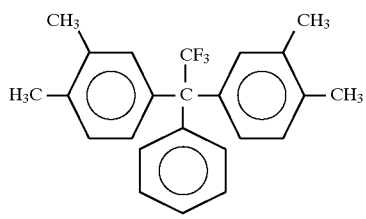

The preferred process additionally comprises utilization of an oxidation catalyst. The preferred oxidation catalyst is potassium permanganate. Especially preferred is when the tetraalkyls are methyls and this process is illustratively shown as follows and is described in Example II.

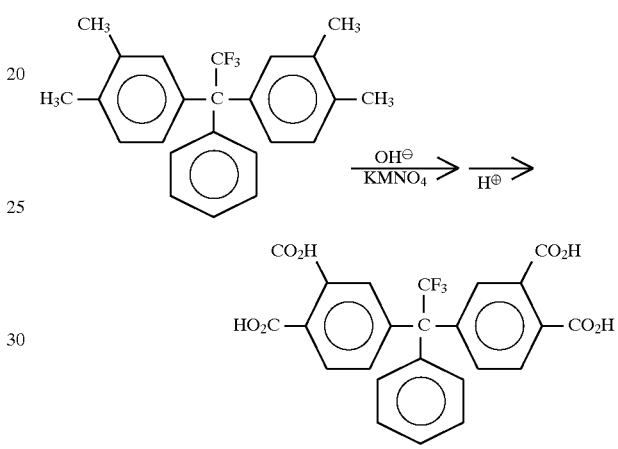

A general description of a typical oxidation process is as follows:

A tetraalkyl substituted 1,1,1-triaryl-2,2,2-trifluoroethane, where one aryl is a phenyl, polycyclic aromatic hydrocarbon or phenyl with a pendant non-alkyl group attached, is oxidized in a two-step oxidation process such as potassium permanganate in pyridine/water followed by in pyridine/alkali or other oxidation processes such as vapor phase oxidation over active metal catalysts such as vanadium pentoxide, or air/liquid phase cobalt acetate/acetic acid oxidations. The permanganate oxidations are done from 50° to 130° C., but typically at the reflux temperature of pyridine/water (~90° C.) for anywhere from 20 minutes to 24 hours, but typically 3 hours. The tetracarboxy product is isolated by acidification of the reaction filtrate and the yields may range from 0 to 100% depending on the ability of the tetraacid to precipitate, but typically are 40 to 70%.

Cyclic Dianhydrides of 1,1,1-Triaryl-2,2,2-Trifluoroethanes

Applicants have also discovered a novel process which comprises conversion of a tetracarboxy-substituted 1,1,1-triaryl-2,2,2-trifluoroethane compound to its new corresponding cyclic dianhydride.

Suitable tetracarboxy-substituted 1,1,1, -triaryl-2,2,2-trifluoroethane compounds are 1,1-bis(dicarboxyaryl)-1-aryl-2,2,2-trifluoroethane compounds. Preferred species include those of the formulae:

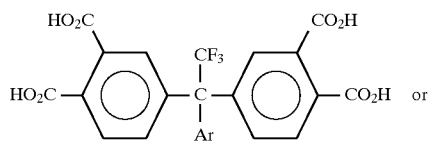

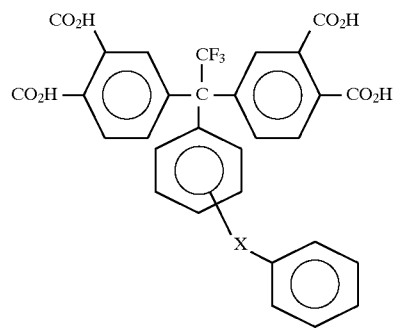

wherein Ar is cyclic and polycyclic aromatics as defined earlier, X is O, S, SO$_2$, NH, PH, N∅, P∅, C=O, CH$_2$ or CH∅. Especially preferred is

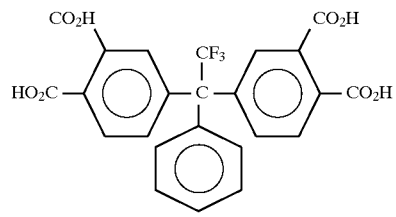

Conversion of the new 3F tetramethyl compound, to the new 3F tetracarboxy intermediate compound, from which the new 3F dianhydride is to be derived, is by customary oxidation procedures with the exception that nitric acid used for similar 6F dianhydrides, pyromellitic dianhydride and benzophenonetetracarboxylic dianhydride cannot be used (due to nitration of the unsubstituted phenyl ring of the tetramethyl 3F precursor). Instead, oxidation to the 3F tetraacid is accomplished by use of an oxidation catalyst which does not cause nitration, such as potassium permanganate, followed by ring closure with acetic anhydride to the 3F dianhydride as described in Example III.

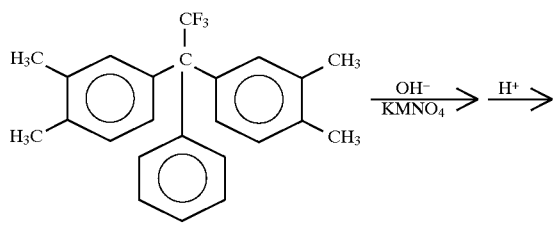

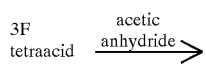

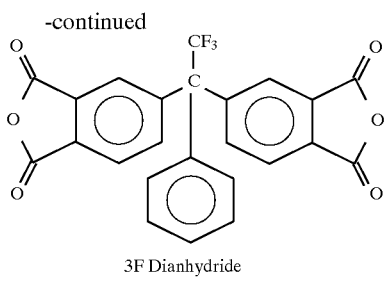

3F Dianhydride

A general description of a typical acetic anhydride dehydration process is as follows:

A tetracarboxy ortho substituted 1,1,1-triaryl-2,2,2-trifluoroethane, where one aryl is a phenyl, polycyclic aromatic hydrocarbon or phenyl with a pendant non-alkyl group attached, is dehydrated to the corresponding dianhydride by treatment in acetic anhydride, with or without acetic acid added, at any temperature between 40° to 120° C., but typically at the reflux temperature of the acetic anhydride/ acetic acid solvent mixture for anywhere from ten minutes to 24 hours, but typically 1–2 hours. The dianhydride is usually isolated by filtration of the cooled reaction solvent and purified by recrystallization and/or sublimation of the reaction product. Additional isolation techniques for soluble dianhydrides are complete evaporation of acetic anhydride/ acetic acid reaction solvent.

This synthetic procedure is analogous to small scale laboratory procedures for other tetramethyl compounds such as tetramethyl compounds with a 6F linkage as disclosed in Example IX of U.S. Pat. No. 3,310,573 or an oxygen connecting linkage as in C. S. Marvel, et al, *J. Am. Chem. Soc.*, 80, 1197 (1958).

Because of the commercial development of 6F dianhydride monomer, improved oxidation processes, rather than permanganate oxidation, have assumedly been long since developed by both E.I. DuPont, American Hoechst and others. These procedures are presumably vapor phase oxidation such as is done for preparation of pyromellitic dianhydride, W. Flavell, et al., Chem. Britian, 3, 375 (1967), or air/liquid phase cobalt acetate/acetic acid type oxidation technology for which American Hoechst is one of the pioneers, or nitric acid oxidation such as used for synthesis of benzophenone tetracarboxylic dianhydride, French Patent 1,346,797 (1963) and 6F dianhydride, British Patent 1,062, 435, Mar. 22, 1967.

In the 3F dianhydride case, only permanganate has been successful as an oxidation reagent. Oxidation with nitric acid also leads to nitration of the unsubstituted phenyl ring of the tetramethyl 3F precursor along with oxidation to the tetraacid. Commercial large scale vapor phase or air/liquid phase oxidations have not been optimized as these entail specialized process development and prior expertise in the technology, although this assumedly would be the most successful as these procedures are used for the preparation of 6F dianhydride from 6F tetramethyl precursor.

BRIEF DESCRIPTION OF DRAWINGS

FIG. 3 illustrates a method for the attachment of a nucleophile substituent onto the previously unsubstituted aryl radical of the tetracarboxy-substituted 1,1,1-triaryl-2,2, 2-trifluoroethane compound.

Diamines of 1,1,1-Triaryl-2,2,2-Trifluoroethane

Applicants have also discovered a novel process which comprises reacting

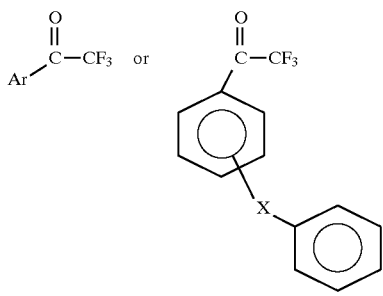

wherein Ar is a cyclic or polycyclic aromatic as defined earlier, X is O, S, SO$_2$, NH, PH, N∅, P∅, C=O, CH$_2$ or CH∅ with aniline or 2,6-substituted or disubstituted anilines

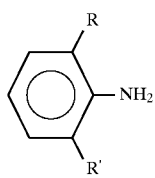

where R and R' are the same or different and stand for hydrogen, methyl, ethyl, propyl, isopropyl, butyl, isobutyl, tert- butyl, and greater alkyls, in the presence of anilinium hydrochloride or the corresponding 2,6-substituted or disubstituted anilinium hydrochloride which produces new diamines of 1,1,1-triaryl-2,2,2-trifluoroethanes having the respective formula as described in Example IV.

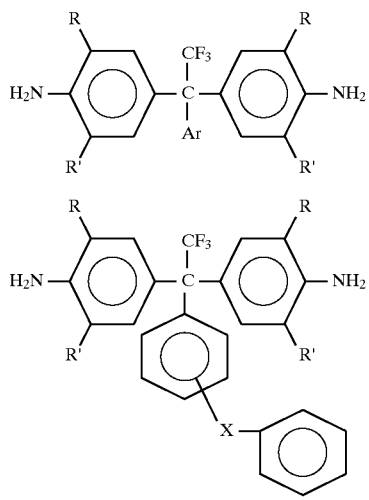

wherein Ar is a cyclic or polycyclic aromatic hydrocarbon as described earlier and X has the same meaning as above and R and R' are the same or different and may stand for H (hydrogen), methyl, ethyl, propyl, isopropyl, butyl, isobutyl, tert-butyl and greater alkyls. The only constraints placed on the aniline or 2,6-substituted or disubstituted anilines being the amine must be liquid at the reaction temperature to act as the reaction solvent.

A general description of a typical aniline or substituted/disubstituted aniline condensation process is as follows:
An aryl trifluoromethyl ketone, where aryl is phenyl, polycyclic aromatic hydrocarbon or phenyl with a pendant non-alkyl group attached, is reacted with excess aniline or excess 2,6-substituted or disubstituted anilines using a stoichiometric or greater amount of a corresponding anilinium or 2,6-substituted or disubstituted anilinium hydrochloride condensation agent, based on moles of aryl trifluoromethyl ketone. The solvent for the reaction is always the aniline or 2-substituted aniline or 2,6-disubstituted aniline. The condensation reaction may be done between 120° to 200° C. but generally at the reflux temperature of the solvent (~160° C.) for anywhere from 1 hour to 7 days but generally 10 to 30 hours. The excess aniline or substituted/disubstituted aniline solvent is removed by steam distillation and the diamine product collected by filtration of the then aqueous reaction. The crude yields may be from 0 to 100%, but generally are quantitative (95–100%). The diamines may be purified by recrystallization from solvents such as ethanol or chloroform, but are not limited to these solvents, with or without charcoal treatment, to provide generally 50 to 85% purified yields of 1,1-bis[(4-amino-3,5-dialkyl)phenyl]-1-phenyl-2,2,2-trifluoroethanes.

Figure 1:
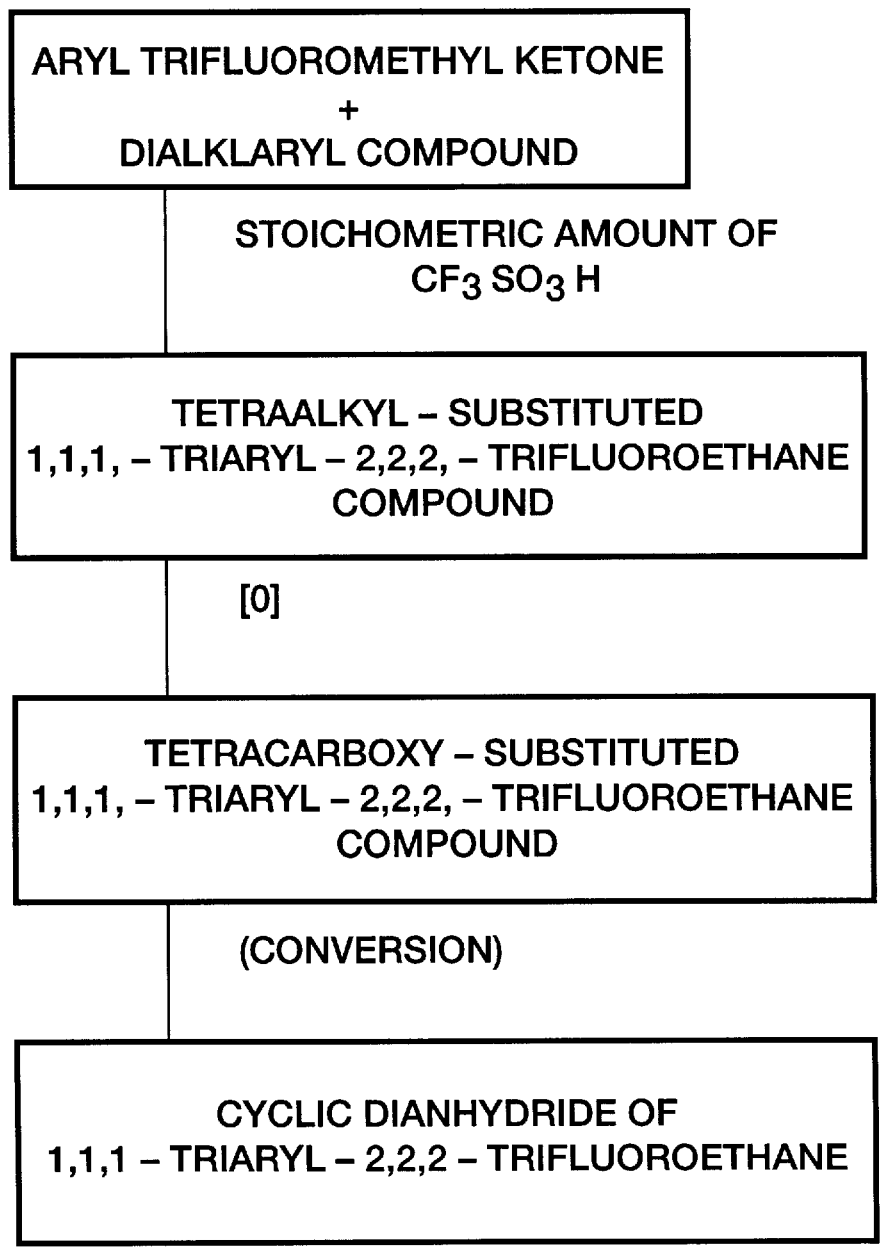
FIG. 1 illustrates the process step of the invention which results in the formation of the novel cyclic anhydride.
Figure 2:
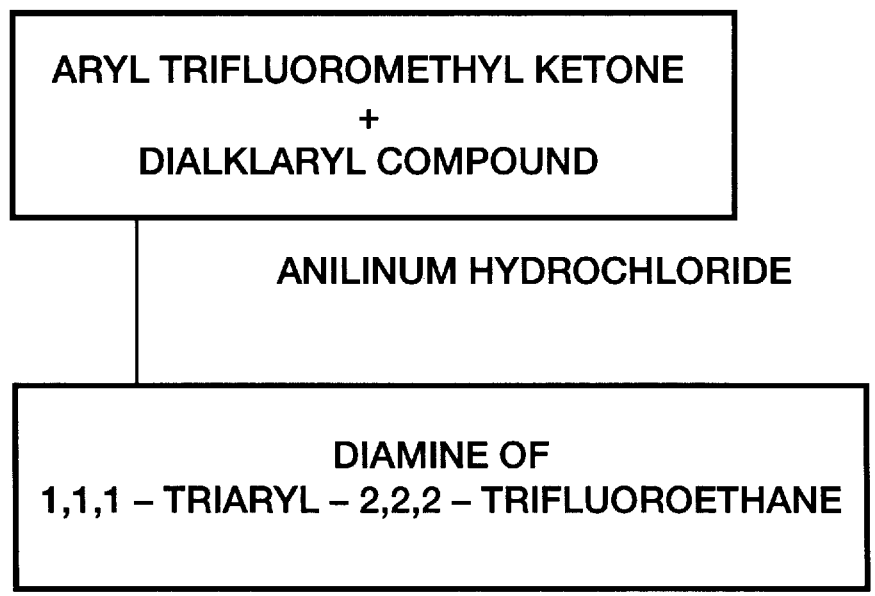
FIG. 2 illustrates a method for preparing a diamine of 1,1,1-triaryl-2,2,2-trifluoroethane.

FIG. 2 illustrates a method for preparing a diamine of 1,1,1-triaryl-2,2,2-trifluoroethane.

Derivatives of Tetracarboxy-Substituted 1,1,1-Triaryl-2,2,2-Trifluoroethane

The applicants claim a novel method for preparing a new compound of the formulae

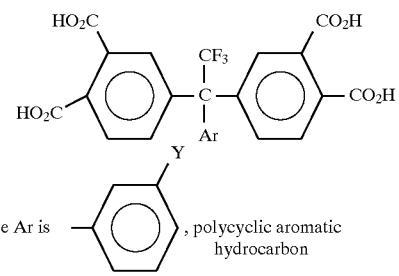

where Ar is 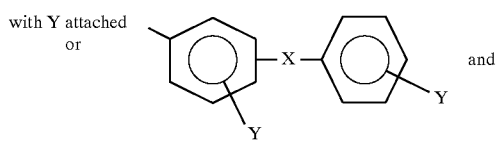, polycyclic aromatic hydrocarbon with Y attached or wherein Y is ∅—O (phenyl-oxygen), ∅—S (phenyl-sulfur), ∅—SO$_2$ (phenyl-sulfone), ∅—PH (phenyl phosphorous hydrogen), ∅$_2$P (diphenyl phosphorous), ∅NH (phenyl nitrogen hydrogen), ∅$_2$N (diphenylnitrogen) or NO$_2$ (nitro). Although (X shown earlier) and some Y may appear equivalent, the distinctions are 1) X may be meta or para while Y is always meta and 2) X is incorporated into the aryl trifluoromethyl ketone before synthesis of the 3F tetraalkyl or 3F diamine compounds while Y is nucleophilicly put on the 3F tetraacid or dianhydride or 3F diamine after the synthesis. The preparation method described comprises oxidation of

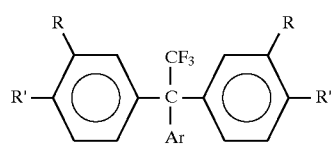

where Ar as described above, R and R' are alkyl as described earlier.

in the presence of HNO₃. Especially preferred is when the oxidized product is the 3-nitro phenyl product shown below and is described in Example V.

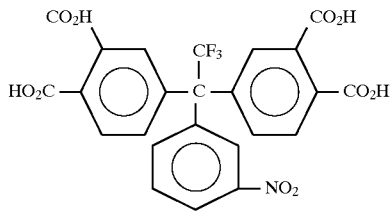

A general description of a typical nitric acid oxidation process is as follows:

A tetraalkyl substituted 1,1,1-triaryl-2,2,2-trifluoroethane, where one aryl is an unsubstituted phenyl, polycyclic aromatic hydrocarbon or phenyl with a pendant non-alkyl group attached, is oxidized in an autoclave with excess 20 to 60% nitric acid, generally 30% to 35% nitric acid, at 120° to 220° C., generally around 180° C. for 30 minutes to 24 hours, generally 1 to 3 hours.

To the reaction mixture is later added up to 5 to 30% by volume of concentrated sulfuric acid, generally 15–20%, and the mixture is heated to 30° to 60° C., generally 50° C., for 30 minutes to 24 hours, generally 2 to 4 hours, to complete the mono-nitration of the unsubstituted 3F aryl rings. The mononitrated tetracarboxy 3F containing products are isolated by filtration of the reaction media and washed with water to provide 40 to 100% yields of product, but generally 90–95% of mono nitro 3F tetraacids. The nitro products are subject to a nucleophilic displacement reaction comprising reacting said oxidized product to Y radical containing nucleophilic reagents, wherein Y has the same meaning as defined above. An example is given in Example VI.

A general description of a typical nucleophilic displacement reaction process is as follows:

A mononitrated tetracarboxy substituted-1,1,1-triaryl-2,2,2-tri-fluoroethane, where one aryl is the mononitrated phenyl, a mononitrated polycyclic aromatic hydrocarbon or a monophenyl with a pendant non-alkyl group as a nitrated or un-nitrated aromatic attached, is reacted with typical nucleophilic reagents, described as Y. The reaction solvents include, but not limited to, N-methyl pyrrolidinone, N-methyl formamide, N,N-dimethyl formamide, N,N-dimethyl acetamide, dimethyl sulfoxide and mixtures thereof. The reaction temperatures may be from room temperature to reflux temperature of the solvent used, but generally reflux temperature. Even higher temperatures may also be attained in an autoclave when nucleophilic substitution has not occurred at reflux temperature. Reaction times and yields vary widely depending on reactivity of the nucleophile and range from 30 minutes to 7 days, but generally 2 to 6 hours to obtain yields ranging from 0 to 100%, but generally 30 to 60%. The nucleophilicly substituted products are isolated by methods of filtration of the precipitated product from the reaction media, addition of water to precipitate the product followed by filtration and/or evaporation of the reaction solvents. Purification is by recrystallization from solvents which include, but are not limited to, ethanol or chloroform or by conversion to the corresponding dianhydride by acetic anhydride treatment and purification of the dianhydride instead.

FIG. 3 illustrates the method for the attachment of a nucleophile substituent onto the previously unsubstituted aryl radical of the tetracarboxy-substituted 1,1,1-triaryl-2,2,2-trifluoroethane compound.

The following examples are intended to illustrate the invention and are not to be construed as limiting the

EXAMPLES

This invention is further illustrated by, but not limited to, the following examples.

Example I

This Example I discloses a method for the preparation of tetraalkyl substituted 1,1,1-triaryl-2,2,2-trifluoroethanes, which comprises reacting an aryl trifluoromethyl ketone with dialkylaryl compound.

In a 500 ml. round bottom flask equipped with a magnetic stir bar and a drying tube was mixed 359 g. (3.38 mole) of o-xylene, 39.5 g. (0.227 mole) of α,α,α,-trifluoroacetophenone and (0.230 mole, slightly more than stoichiometric based on aryl trifluoromethyl ketone moles) of trifluoromethane sulfonic acid. For larger scale reactions, the trifluoromethane sulfonic acid is added dropwise over 1–2 hours and the reaction is initially placed in an ice bath, then left to reach room temperature during the addition. The solution was stirred at room temperature for 48 hours during which the product precipitated. After this time, the product was collected by suction filtration, rinsed with o-xylene, followed by three rinsings with water. The filtrate was extracted in a separatory funnel with successive washings with water, aqueous sodium bicarbonate and water. The o-xylene solution was dried over magnesium sulfate, filtered, evaporated to about 50 ml. ant placed in a refrigerator to obtain additional crystalline product, which was collected by suction filtration. The 1,1-bis[4-(1,2-dimethyl) phenyl]-1-phenyl-2,2,2-trifluoroethane was recrystallized from a 90/10 by volume mixture of heptane/benzene to yield from initial reaction precipitate, 57.2 g. (68.5% yield) of white solid, m.p. 177°–178° C. and 4.8 g (5.7% yield) of white solid, m.p. 171°–174° C. from the solution after evaporation of the o-xylene reaction solvent.

Example II

This Example II discloses a method for the preparation of tetracarboxy-substituted 1,1,1-triaryl-2,2,2-trifluoroethanes, which comprises oxidation of tetraalkyl-substituted 1,1,1-triaryl-2,2,2-trifluoroethanes.

In a 500 ml. 3-neck round bottom flask equipped with a magnetic stir bar and a reflux condenser was mixed 10.00 g. (27.2 mmoles) of 1,1-bis[4-(1,2-dimethyl)phenyl]-1-phenyl-2,2,2-trifluoroethane and 225 ml of pyridine. The mixture was brought to reflux temperature and 50 ml of water was added. Then 21.48 g (0.136 moles, 5 fold excess) of solid potassium permanganate was added in small portions over 10 minutes. After 3 hours stirring at reflux temperature, the manganese dioxide formed was collected by filtration through Celite and washed with water/pyridine. The yellow filtrate was evaporated to 50 ml., placed back in the 500 ml. flask with 200 ml. of water and 16 g. (0.4 moles) of sodium hydroxide and heated to reflux temperature. Then 25.8 g. (0.163 mole, 6 fold excess) of potassium permanganate was added in small portions over 5–10 minutes. After 3 hours stiring at reflux temperature, 10 ml. of ethanol was added cautiously to consume the excess potassium permanganate and the resultant manganese dioxide was again collected by filtration through Celite and washed with 50 ml. of hot water. The filtrate was evaporated to ~100 ml. (until the pyridine odor is gone) and acidified with 250 ml. of 2N hydrochloric acid. The gummy precipitate was cooled in freezer overnight until crystals formed. The crystals were collected by filtration and air dried in 80° C. oven to obtain 8.54 g. (64.3% yield) of 1,1-bis[4-(1,2-dicarboxy)phenyl]-1-phenyl-2,2,2-trifluoroethane, m.p. ~122° C.

Example III

This Example III discloses a method for the preparation of cyclic dianhydrides of 1,1,1-triaryl-2,2,2-trifluoroethanes which comprises dehydration of tetracarboxy substituted 1,1,1-triaryl-2,2,2-trifluoroethanes.

In a 50 ml. round bottom flask equipped with a magnetic stirrer and a reflux condenser was mixed 1.50 g. (3.07 mmoles) of the crude tetraacid (from Example II), 1,1-bis[4-(1,2-dicarboxy)phenyl]-1-phenyl-2,2,2-trifluoroethane and 5.4 g. (0.053 moles) of acetic anhydride and 5 ml. of acetic acid. The stirred solution was heated at reflux temperature for 1.5 hours, and then evaporated to dryness to yield 1.21 g. (87% yield) of crude dianhydride, m.p. ~208° C. Attempts to recrystallize the dianhydride from acetic anhydride or heptane/benzene only yielded white dianhydride, m.p. 204°–206° C., and all samples were quite hygroscopic. Consequently, the dianhydride of 1,1-bis-[4-(1,2-dicarboxy)-phenyl]-1-phenyl-2,2,2-trifluoroethanes was vacuum dried at 60° C. and used as isolated.

Example IV

This Example IV discloses a method for the preparation of diamines of 1,1,1-triaryl-2,2,2-trifluoroethanes, which comprises reacting an aryltrifluoromethyl ketone with an aniline or substituted anilines or disubstituted anilines.

In a 500 ml. round bottom flask equipped with a magnetic stirrer and a reflux condensor was mixed 186 g. (2.0 moles) of aniline, 46.7 g. (0.268 mole) of α,α,α-trifluoroacetophenone and 50.0 g. (0.368 mole) of aniline hydrochloride. The stirred mixture was heated to 160° C. for 20 hours. The reaction was then cooled to below 120° C. and 40 g. (0.47 mole) of sodium bicarbonate slurried in 100 ml. of water was added cautiously in small portions. The purple solution was then steam distilled to recover ~¾ of the aniline, during which purple solid formed in the flask. The purple solid was collected by suction filtration, washed 3 times with 150 ml. of water and air dried to give 88.5 g. (97.4% yield) of purple solid m.p. 200°–205° C. The diamine product is recrystallized from chloroform or 95% ethanol with charcoal treatments to remove the color to yield 77.3 g. (84.2% yield) of white 1,1-bis(4-aminophenyl)-1-phenyl-2,2,2-trifluoroethane, m.p. 217°–217.5° C. This specific reaction has been done 6 times on scales starting from 10 to 100 g. of α,α,α-trifluoroacetophenone and consistently provides nearly quantitative yields and 70 to 85% purified yields.

Example V

This Example V discloses a method for the preparation of nitrated tetracarboxy substituted 1,1,1-triaryl-2,2,2-trifluoroethanes, which comprises nitric acid oxidation of tetraalkyl substituted 1,1,1-triaryl-2,2,2-trifluoroethanes.

In an autoclave is mixed 10.0 g. (27.2 mmoles) of 1,1-bis-[4-(1,2-dimethyl)phenyl]-1-phenyl-2,2,2-trifluoroethane and 180 g. of 35% nitric acid. The mixture is heated in the sealed autoclave for 2 hours at 180° C. and cooled to room temperature. The tetraacid (with some nitration on the 3F phenyl ring) is seen as a precipitate in the nitric acid reaction media. To this mixture is added cautiously 30 g. of concentrated sulfuric acid and the mixture is heated to at least 50° C. for 2 hours, in order to completely mononitrate the 3F phenyl ring. The reaction is cooled to room temperature and the precipitate is collected by filtration, water washed and air dried to yield greater than 90% yields of 1,1-bis-[4-(1,2-dicarboxy)phenyl]-1-(3-nitrophenyl)-2,2,2-trifluoroethane.

Example VI

This Example VI discloses a method for the preparation of tetracarboxy substituted 1,1,1-triaryl-2,2,2-trifluoroethanes with pendant fragments on one phenyl ring, which comprises nucleophilic displacement reactions in the nitric acid oxidation products of tetraalkyl substituted 1,1,1-triaryl-2,2,2-trifluoroethanes.

In a 500 ml. round bottom flask equipped with a magnetic stir bar and a reflux condenser is mixed 10.0 g. (24.2 mmoles) of 1,1-bis[4-(1,2-dicarboxy)phenyl]-1-(3-nitrophenyl)-2,2,2-trifluoroethane 3.0 g. (25.8 mmoles, 7% excess) of sodium phenoxide and 100 ml. of N,N-dimethylformamide. The stirred mixture is heated to the reflux temperature for 3 hours and cooled to room temperature. To the solution is added 40 ml. of water and the precipitated 1,1-bis[4-(1,2-dicarboxy)phenyl]-1-(3-phenoxyphenyl)-2,2,2-trifluoroethane is collected by filtration, washed with water and air dried.

What is claimed is:

1. A compound 1,1-bis(dialkylaryl)-1-aryl-2,2,2-trifluoroethane.

2. A compound according to claim 1, which is selected from the formulae:

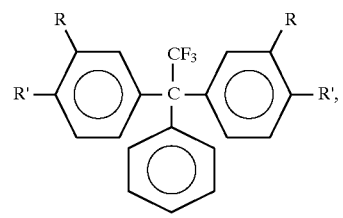

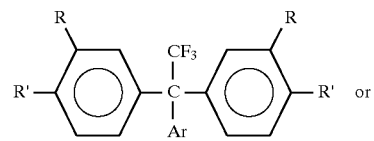 or

-continued
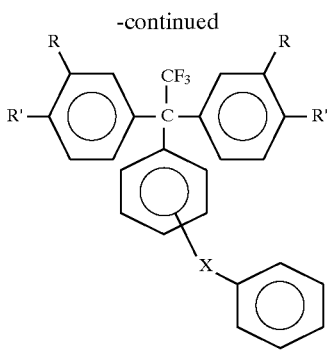
wherein Ar is phenyl or a polycyclic aromatic hydrocarbon and X is O, S, SO₂, NH, PH, NØ, pØ, C=O, CH₂ or CHØ, and R and R' are the same or different and are individually an alkyl radical.
3. A compound according to claim 2, which is
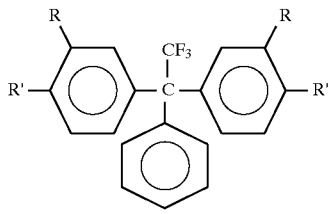
wherein R and R' are the same or different and are individually an alkyl radical.
* * * * *